United States Patent [19]

Commercon et al.

[11] Patent Number: 5,726,318
[45] Date of Patent: Mar. 10, 1998

[54] PROCESS FOR THE PREPARATION OF TAXANE DERIVATIVES

[75] Inventors: Alain Commercon, Vitry-sur-Seine; Eric Didier, Paris; Elie Fouque, Saint Maur Des Fosses, all of France

[73] Assignee: Rhone-Poulenc Rorer S.A., Antony, France

[21] Appl. No.: 778,637

[22] Filed: Jan. 3, 1997

Related U.S. Application Data

[62] Division of Ser. No. 411,690, filed as PCT/FR93/00969, Oct. 4, 1993, Pat. No. 5,621,121.

[30] Foreign Application Priority Data

Oct. 5, 1992 [FR] France .................. 92 11743

[51] Int. Cl.$^6$ .................. C07D 263/06; C07D 305/14
[52] U.S. Cl. .................. 548/215; 549/510; 549/511
[58] Field of Search .................. 548/215; 549/510, 549/511

[56] References Cited

U.S. PATENT DOCUMENTS

| | | | |
|---|---|---|---|
| 5,319,112 | 6/1994 | Kingston et al. | 549/510 |
| 5,556,878 | 9/1996 | Kelly et al. | 514/449 |
| 5,580,997 | 12/1996 | Bouchard et al. | 549/510 |

FOREIGN PATENT DOCUMENTS

WO 92/09589  6/1992  WIPO.

OTHER PUBLICATIONS

Guéritte-Voegelein et al. "Relationships between the structure of Taxol Analogues and Their Antimitotic Activity", J. Med. Chem. 1991, 34, 992–998.

*Primary Examiner*—Ba K. Trinh
*Attorney, Agent, or Firm*—Finnegan, Henderson, Farabow, Garrett & Dunner, L.L.P.

[57]  ABSTRACT

This invention relates to a method of preparing taxane derivatives of formula (I) by esterification of protected baccatin III or 10-deacetylbaccatin III by means of an acid of formula (VII), elimination of protection groupings and acylation of the amine function of the side chain. The products of formula (I) have remarkable antitumor and antileukemia properties. In formulae (I) and (VII): Ar stands for aryl, R is hydrogen or acetyl, $R_1$ is a benzoyl radical or an $R_2$—O—CO— radical in which $R_2$ is alkyl, alkenyl, alkynyl, cycloalkyl, cycloalkenyl, bicycloalkyl, phenyl or heterocyclyl, $R_3$ is a trihalomethyl radical or phenyl substituted by a trihalomethyl radical, $R_4$ is a hydrogen atom or is the same as $R_1$.

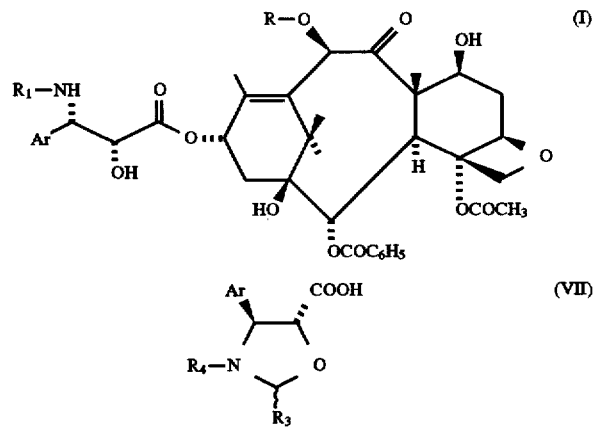

6 Claims, No Drawings

5,726,318

PROCESS FOR THE PREPARATION OF TAXANE DERIVATIVES

This is a Rule 60 Divisional of application Ser. No. 08/411,690, filed as PCT/FR93/00969, Oct. 4, 1993, now U.S. Pat. No. 5,621,121.

DESCRIPTION OF THE INVENTION

The present invention relates to a new process for the preparation of taxane derivatives of general formula:

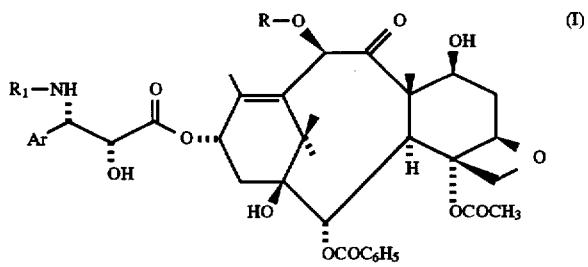

which have notable antileukaemic and antitumour properties.

In the general formula (I), R represents a hydrogen atom or an acetyl radical, $R_1$ represents a benzoyl radical or a radical $R_2$—O—CO— in which $R_2$ represents an alkyl, alkenyl, alkynyl, cycloalkyl, cycloalkenyl, bicycloalkyl, phenyl or nitrogen-containing heterocyclyl radical, and Ar represents an aryl radical.

More particularly, R represents a hydrogen atom or an acetyl radical and $R_1$ represents a benzoyl radical or a radical $R_2$—O—CO— in which $R_2$ represents:

a straight or branched alkyl radical containing 1 to 8 carbon atoms, an alkenyl radical containing 2 to 8 carbon atoms, an alkynyl radical containing 3 to 8 carbon atoms, a cycloalkyl radical containing 3 to 6 carbon atoms, a cycloalkenyl radical containing 4 to 6 carbon atoms or a bicycloalkyl radical containing 7 to 10 carbon atoms, these radicals optionally being substituted by one or a number of substituents chosen from the halogen atoms and the hydroxyl radical, alkyoxy radical containing 1 to 4 carbon atoms, dialkylamino radical, each alkyl part of which contains 1 to 4 carbon atoms, piperidino radical, morpholino radical, 1-piperazinyl radical (optionally substituted in the 4-position by an alkyl radical containing 1 to 4 carbon atoms or by a phenylalkyl radical, the alkyl part of which contains 1 to 4 carbon atoms), cycloalkyl radical containing 3 to 6 carbon atoms, cycloalkenyl radical containing 4 to 6 carbon atoms, phenyl radical, cyano radical, carboxyl radical or alkyloxycarbonyl radical, the alkyl part of which contains 1 to 4 carbon atoms, or a phenyl radical optionally substituted by one or a number of atoms or radicals chosen from the alkyl radicals containing 1 to 4 carbon atoms or the alkyloxy radicals containing 1 to 4 carbon atoms, or a saturated or unsaturated nitrogen-containing heterocyclyl radical containing 5 or 6 members, optionally substituted by one or a number of alkyl radicals containing 1 to 4 carbon atoms, it being understood that the cycloalkyl, cycloalkenyl or bicycloalkyl radicals may optionally be substituted by one or a number of alkyl radicals containing 1 to 4 carbon atoms, and Ar represents a phenyl or α- or β-naphthyl radical optionally substituted by one or a number of atoms or radicals chosen from the halogen atoms (fluorine, chlorine, bromine or iodine) and the alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano and trifluoromethyl radicals, it being understood that the alkyl radicals and the alkyl portions of the other radicals contain 1 to 4 carbon atoms, that the alkenyl and alkynyl radicals contain 3 to 8 carbon atoms and the aryl radicals are phenyl or α- or β-naphthyl radicals.

The products of general formula (I) in which k represents a hydrogen atom or an acetyl radical, $R_1$ represents a benzoyl or t-butoxycarbonylamino radical and Ar represents a phenyl radical are very particularly advantageous.

The products of general formula (I) in which $R_1$ represents a benzoyl radical correspond to taxol and to 10-deacetyltaxol and the products of general formula (I) in which $R_1$ represents a t-butoxycarbonyl radical correspond to those which form the subject of European Patent EP 0,253,738.

According to the process which is described in International Application PCT WO 92/09589, the derivatives of general formula (I) can be obtained by:

condensation of a derivative of the oxazolidine of general formula:

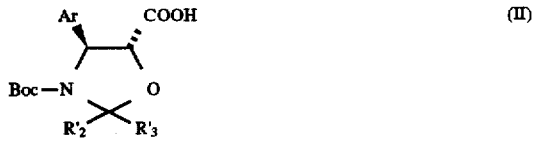

in which Ar is defined as above, Boc represents the t-butoxycarbonyl radical and $R'_2$ and $R'_3$, which are identical or different, represent an alkyl radical containing 1 to 4 carbon atoms, optionally substituted by one or a number of aryl radicals, or an aryl radical, or else $R'_2$ and $R'_3$ form, together with the carbon atom to which they are bonded, a ring having from 4 to 7 members, with the protected baccatin III or 10-deacetylbaccatin (III of general formula:

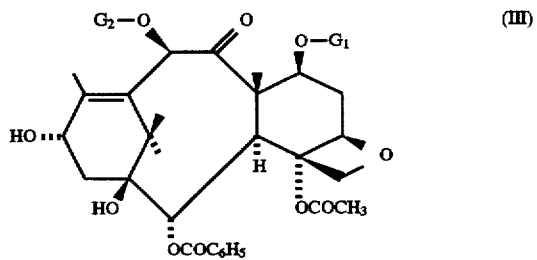

in which $G_1$ represents a protective group of the hydroxyl functional group and $G_2$ represents an acetyl radical or a protective group of the hydroxyl functional group, to produce a product of general formula:

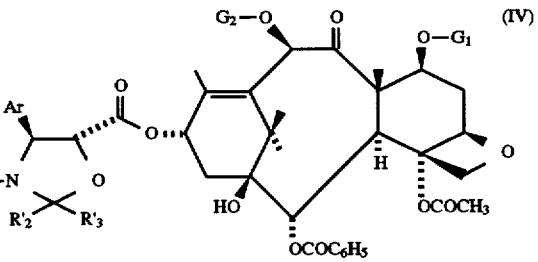

in which Ar, $R'_2$, $R'_3$, $G_1$, $G_2$ and Boc are defined as above, treatment in acidic medium of the product of general formula (IV) under conditions which are without effect on $G_1$ and $G_2$ to produce the product of general formula:

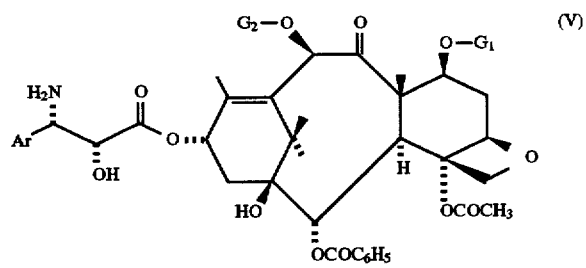

(V)

in which Ar, $G_1$ and $G_2$ are as defined above, treatanent of the product of general formula (V) with a reagent suitable for introducing a radical $R_1$, that is to say a benzoyl or $R_2$—O—CO— radical, to produce a product of general formula:

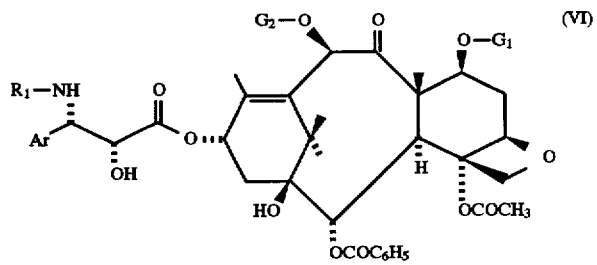

(VI)

in which Ar, $R_1$, $G_1$ and $G_2$ are defined as above, and replacement of the protective groups $G_1$ and $G_2$ of the product of general formula (VI) by hydrogen atoms to produce the product of general formula (I).

It has now been found, and it is this which forms the subject of the present invention, that the products of general formula (I) can be obtained:

1) by esterifying the protected baccatin III or 10-deacetylbaccatin III of general formula (III), in which $G_1$ and optionally $G_2$ represent a protective group of the hydroxyl functional group, using an acid of general formula:

(VII)

in which Ar is defined as above, $R_3$ represents a trihalomethyl, preferably trichloromethyl radical or a phenyl radical substituted by a trihalomethyl, preferably trichloromethyl radical, or of a derivative of this acid, and $R_4$ represents a hydrogen atom or is identical to $R_1$ defined as above, to produce a product of general formula:

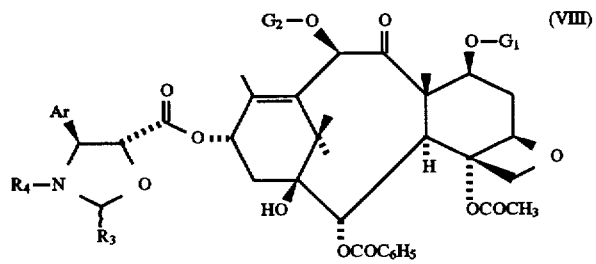

(VIII)

in which Ar, $R_3$, $R_4$, $G_1$ and $G_2$ are defined as above, 2) by replacing protective groups of the hydroxyl and amino functional groups of the product of general formula (VIII) by hydrogen atoms to produce the product of formula:

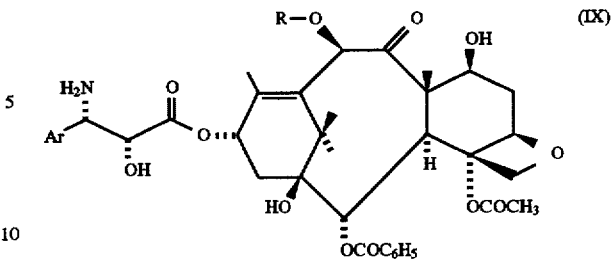

(IX)

3) by treating the product obtained of general formula (IX) with a reagent which makes it possible to introduce a substituent $R_1$ onto the amino functional group to produce a product of general formula (I).

According to the present invention, esterification of the protected baccatin III or of the protected 10-deacetylbaccatin III of general formula (III) with an acid of general formula (VII), in which $R_4$ preferably represents a hydrogen atom, can be carried out in the presence of a condensation agent such as a diimide, such as dicyclohexylcarbodiimide, or a reactive carbonate such as di-2-pyridyl ketone and of an activating agent such as an aminopyridine, such as 4-dimethylaminopyridine or 4-pyrrolidinopyridine, the reaction being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between −10° and 90° C. It is particularly advantageous to carry out the esterification in an aromatic hydrocarbon at a temperature in the region of 20° C.

The esterification can also be carried out by using the acid of general formula (VII) in the anhydride form of general formula:

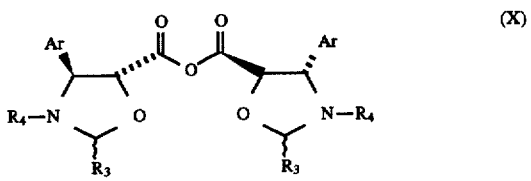

(X)

in which Ar, $R_3$ and $R_4$ are defined as above, in the presence of an activating agent such as an aminopyridine, such as 4-dimethylaminopyridine or 4-pyrrolidinopyridine, the reaction being carried out in an organic solvent chosen from ethers such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 0° and 90° C.

The esterification can also be carried out by using the acid of general formula (VII) in the halide form or mixed anhydride form of general formula:

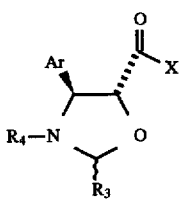

(XI)

in which Ar, $R_3$ and $R_4$ are defined as above, $R_4$ preferably representing a hydrogen atom, and X represents a halogen atom or an acyloxy or aroyloxy radical, optionally prepared in situ, in the presence of a base which is preferably a nitrogenous organic base such as a tertiary aliphatic amine, a pyridine or an aminopyridine such as 4-dimethylaminopyridine or 4-pyrrolidinopyridine, the reaction being carried out in an inert organic solvent chosen from ethers such as tetrahydrofuran, diisopropyl ether, methyl t-butyl ether or dioxane, ketones such as methyl t-butyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane and aromatic hydrocarbons such as benzene, toluene, xylenes, ethylbenzene, isopropylbenzene or chlorobenzene, at a temperature between 10° and 80° C., preferably in the region of 20° C.

Preferably, an activated derivative of general formula (XI) is used in which X represents a halogen atom or an acyloxy radical containing 1 to 5 carbon atoms or an aryloxy radical in which the aryl part is a phenyl radical optionally substituted by 1 to 5 atoms or radicals, which are identical or different, chosen from halogen atoms (chlorine, bromine) and nitro, methyl or methoxy radicals.

Replacement by hydrogen atoms of the protective groups of the hydroxyl and amino functional groups of the product of general formula (VIII), in which, preferably, $G_1$ and optionally $G_2$ represent a 2,2,2-trichloroethoxycarbonyl or 2-(2-(trichloromethyl)propoxy)carbonyl radical, is generally carried out by treatment with zinc, optionally in combination with copper, in the presence of acetic acid at a temperature between 20° and 60° C. or using an inorganic or organic acid, such as hydrochloric acid or acetic acid in solution in an aliphatic alcohol containing 1 to 3 carbon atoms or in an aliphatic ester (ethyl acetate, isopropyl acetate, n-butyl acetate) in the presence of zinc, optionally in combination with copper.

Replacement of the protective groups of the product of general formula (VIII) by hydrogen atoms can also be carried out by electrolytic reduction.

The introduction of a substituent $R_1$ onto the amino functional group of the product of general formula (IX) is carried out by reacting with benzoyl chloride or with the reactive derivative of general formula:

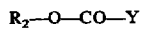

$R_2$—O—CO—Y      (XII)

in which $R_2$ is defined as above and Y represents a halogen atom or a residue —O—$R_2$ or —O—CO—$R_2$, the reaction being carried out in an organic solvent such as an aliphatic ester, such as ethyl acetate, or an alcohol, such as methanol, ethanol, isopropanol or n-butanol, or a halogenated aliphatic hydrocarbon, such as dichloromethane, in the presence of an inorganic or organic base, such as sodium bicarbonate. Generally, the reaction is carried out at a temperature between 0° and 50° C., preferably in the region of 20° C.

The acid of general formula (VII) can be obtained by saponification in basic medium of the ester of general formula:

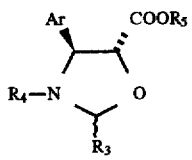

(XIII)

in which Ar, $R_1$ and $R_4$ are defined as above and $R_5$ represents an alkyl radical containing 1 to 4 carbon atoms optionally substituted by a phenyl radical.

Generally, the saponification is carried out using an inorganic base such as an alkali metal hydroxide (lithium, potassium, sodium) or an alkali metal carbonate or bicarbonate (sodium bicarbonate, potassium carbonate or potassium bicarbonate) in aqueous/alcohol medium, such as a methanol/water mixture, at a temperature between 10° and 40° C., preferably in the region of 20° C.

The ester of general formula (XIII) can be obtained by reacting an aldehyde of general formula:

$R_3$—CHO      (XIV)

in which $R_3$ is defined as above, optionally in the form of a dialkyl acetal, with a phenylisoserine derivative of general formula:

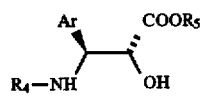

(XV)

in which Ar, $R_4$ and $R_5$ are defined as above, in the racemic form or, preferably, in the 2R,3S form, the reaction being carried out in an inert organic solvent in the presence of a strong inorganic acid, such as sulphuric acid, or organic acid, such as p-toluenesulphonic acid, optionally in the pyridinium salt form, at a temperature between 0° C. and the boiling temperature of the reaction mixture. Solvents which are particularly well suited are aromatic hydrocarbons.

The product of general formula (XV) can be prepared under the conditions described or by adaptation of the methods described in International Application PCT WO 92/09589.

The anhydride of general formula (X) can be obtained by reacting a dehydrating agent, such as dicyclohexylcarbodiimide, with the acid of general formula (VII), the reaction being carried out in an organic solvent chosen from ethers, such as tetrahydrofuran, diisopropyl ether, methyl t-butyl ether or dioxane, ketones such as methyl isobutyl ketone, esters such as ethyl acetate, isopropyl acetate or n-butyl acetate, nitriles such as acetonitrile, aliphatic hydrocarbons such as pentane, hexane or heptane, halogenated aliphatic hydrocarbons such as dichloromethane or 1,2-dichloroethane, and aromatic hydrocarbons such as benzene, toluene, xylenes, ethylbenzene, isopropylbenzene or chlorobenzene, at a temperature between 0° and 30° C.

The activated acid of general formula (XI) can be obtained by reacting a sulphuryl halide, preferably the chloride, or a product of general formula:

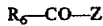

$R_6$—CO—Z      (XVI)

in which $R_4$ represents an alkyl radical containing 1 to 4 carbon atoms or a phenyl radical optionally substituted by 1

7 to 5 atoms or radicals, which are identical or different, chosen from halogen atoms and nitro, methyl or methoxy radicals and Z represents a halogen atom, preferably a chlorine atom, with an acid of general formula (VII), the reaction being carried out in a suitable organic solvent, such as tetrahydrofuran, in the presence of an organic base, such as a tertiary amine such as triethylamine, at a temperature between 0° and 30° C.

EXAMPLES

The following example illustrates the present invention.

Example 0.21 g of dicyclohexylcarbodiimide is added, at a temperature in the region of 20° C., to a solution of 0.33 g of (4S,5R)-4-phenyl-2-trichloromethyl-1,3-oxazolidine-5-carboxylic acid, of 0.49 g of 4-acetoxy-2α-benzoyloxy-5β, 20-epoxy-1,13α-dihydroxy- 9-oxo-7β,10β-bis(2,2,2-trichloroethoxy)carbonyloxy-11-taxene and of 0.013 g of 4-dimethylaminopyridine in 2.77 cm³ of anhydrous toluene. The solution is stirred at 25° C. for 2–3 hours and the dicyclohexylurea formed is then filtered through a sintered glass. The precipitate is rinsed with 20 cm³ of ethyl acetate and the organic phase is washed successively with 20 cm³ of a molar aqueous hydrochloric acid solution, 20 cm³ of a saturated aqueous sodium bicarbonate solution and 10 cm³ of a saturated aqueous sodium chloride solution. The organic phase is dried over sodium sulphate and concentrated to dryness under reduced pressure to give 0.78 g of crude product which is purified by filtration through 20 g of silica gel, the eluent being an ethyl acetate/n-hexane (v/v=4/6) mixture. After concentrating to dryness under reduced pressure, there is obtained 0.70 g of 4-acetoxy-2α-benzoyloxy-5β,20-epoxy-1-hydroxy-9-oxo-7β,10β-bis(2,2,2-trichloroethoxy) carbonyloxy-11-taxene-13α-yl (4R, 5S)-4-phenyl-2-trichloromethyl-1,3-oxazolidine-5-carboxylate in the form of a mixture of two diastereoisomers whose characteristics are the following:

infrared spectrum (as a pellet with KBr): main characteristic absorption bands at 1760, 1730, 1600, 1585, 1490, 1450, 1250, 1065, 980, 810, 760, 725–700 cm$^{-1}$ proton nuclear magnetic resonance spectrum (400 MHz; CDCl$_3$; chemical shifts δ in ppm; coupling constants J in Hz) (mixture of diastereoisomers in the proportions 70/30); 1.15 to 1.30 (mt, 6H), 1.84 (s, 1H), 1.86 (s, 1H), 2.07 (s, 1H), 2.00 to 2.10 (mt, 1H), 2.15 (s, 1H), 2.10 to 2.30 (mt, 2H), 2.55 to 2.70 (mt, 1H), 3.20 (large unresolved peak, 1H), 3.32 (large unresolved peak, 1H), 3.87 (d, J=7, 1H), 3.94 (d, J=7, 1H), 4.10 (d, J=8, 1H), 4.13 (d, J=8, 1H), 4.27 (d, J=8, 1H), 4.30 (d, J=8, 1H), 4.58 (d, J=7.5, 1H), 4.61 (d, J=12, 1H), 4.63 (d, J=12, 1H), 4.70 (d, J=8, 1H), 4.80 (AB, 2H), 4.80 (mt, 1H), 4.85 to 5.00 (mt, 2H), 5.13 (d, J=7.5, 1H), 5.53 (broad s, 1H), 5.56 (dd, J=11 and 7, 1H), 5.60 (dd, J=11 and 7, 1H), 5.66 (d, J=7, 1H), 5.68 (d, J=7, 1H), 6.20 to 6.35 (mt, 1H), 6.24 (s, 1H), 6.27 (s, 1H), 7.30 to 7.50 (mt, 3H), 7.30 to 7.70 (mt, 3H), 7.60 (d, 2H), 8.03 (d, J=7.5, 2H).

0.27 g of zinc powder and 1.07 cm³ of acetic acid are added to a solution of 0.50 g of 4-acetoxy-2α-benzoyoxy-5β, 20-epoxy-1-hydroxy-9-oxo-7β, 10β-bis(2,2,2-trichloroethoxy)carbonyloxy-11-taxen-13α-yl (4S,5R)-4-phenyl-2-trichloromethyl-1,3-oxazolidine-5-carboxylate in 5 cm³ of ethyl acetate. The solution is stirred at a temperature in the region of 20° C. for 15 hours and then filtered through a sintered glass. The precipitate is washed with ethyl acetate (20 cm³) and the organic phase is washed successively with water (15 cm³) and with a saturated aqueous sodium bicarbonate solution (2 times 15 cm³) and then dried over sodium sulphate. The solution is then concentrated to dryness under reduced pressure at 35° C. to give 0.33 g of an amorphous solid. Quantitative determination by high performance liquid chromatography shows that 4-acetoxy-2α-benzoyloxy-5β, 20-epoxy-1,7β, 10β-trihydroxy-9-oxo-11-taxen-13α-yl (2R,3S)-3-amino-3-phenyl-2-hydroxypropionate, assaying at 50%, is obtained with a yield of 65%.

The characteristics of the product obtained are the following:

proton nuclear magnetic resonance spectrum (400 MHz; d$_6$-DMSO; chemical shifts δ in ppm; coupling constants J in Hz): 0.99 (s, 3H), 1.03 (s, 3H), 1.53 (s, 3H), 1.65 (mt, 1H), 1.75 (s, 3H), 1.70 to 1.90 (mt, 2H), 2.12 (s, 3H), 2.28 (mt, 1H), 3.65 (d, J=7, 1H), 4.02 (AB, J=8, 2H), 4.00 to 4.15 (mt, 3H), 4.56 (s, 1H), 4.90 (broad d, J=10, 1H), 4.99 (broad s, 1H), 5.05 (large unresolved peak, 1H), 5.10 (s, 1H), 5.42 (d, J=7, 1H), 5.88 (t, J=9, 1H), 7.15 to 7.45 (mt, 5H), 7.65 (t, J=7.5, 2H), 7.73 (t, J=7.5, 1H), 7.98 (d, J=7.5, 2H).

0.11 g of di-tert-butyl dicarbonate is added to a solution of 0.30 g of crude 4-acetoxy-2α-benzoyloxy- 5β,20-epoxy-1,7β,10β-trihydroxy-9-oxo-11-taxen-13α-yl (2R,3S)-3-amino-3-phenyl-2-hydroxypropionate, obtained above, in 5 cm³ of methanol. The reaction mixture is stirred at a temperature in the region of 20° C. for 15 hours, and then 20 cm³ of water are added. The solution is extracted three times with 15 cm³ of methylene chloride. The combined organic phases are dried over sodium sulphate and then concentrated to dryness under reduced pressure. 0.395 g of crude product is thus obtained. Quantitative determination by high performance liquid chromatography shows that the 4-acetoxy-2α-benzoyloxy-5β,20-epoxy-1,7β,10β-trihydroxy-9-oxo-11-taxen-13α-yl (2R,3S)-3-(tert-butoxycarbonylamino)-3-phenyl-2-hydroxypropionate yield is 70%.

(4S,5R)-4-Phenyl-2-trichloromethyl-1,3-oxazolidine-5-carboxylic acid can be prepared in the following way:

A solution of 3.0 g of methyl (2R,3S)-3-(tert-butoxycarbonylamino)-2-hydroxy-3-phenylpropionate, of 5 cm³ of chloral and of 0.05 g of pyridinium p-toluenesulphonate in 40 cm³ of anhydrous toluene is heated at reflux with distillation of the solvent. 15 cm³ of solvent are distilled and then 5 cm³ of chloral and 0.05 g of pyridinium p-toluenesulphonate are added. 20 cm³ of solvent are distilled and then 5 cm³ of chloral as well as 30 cm³ of anhydrous toluene are added. 25 cm³ of solvent are distilled and 5 cm³ of chloral and 35 cm³ of anhydrous toluene are added. 25 cm³ of solvent are distilled and then the solution is cooled to a temperature in the region of 20° C. The organic solution is washed with water (2 times 50 cm³), dried over sodium sulphate and concentrated to dryness under reduced pressure at approximately 50° C. The residue obtained is purified by liquid chromatography on silica gel, the eluent being an ethyl acetate/cyclohexane (1/3 by volume) mixture. There are thus obtained, with a yield of 91%, 3.0 g of (4S,5R)-5-methoxycarbonyl-4-phenyl-2-trichloromethyl-1,3-oxazolidine whose characteristics are the following:

infrared spectrum (CCl$_4$): characteristic absorption bands at 3400, 3100, 3075, 3040, 2960, 1755, 1605, 1590, 1495, 1460, 1440, 1205 and 700 cm$^{-1}$ proton nuclear magnetic resonance spectrum (200 MHz; d$_6$-DMSO; chemical shifts δ in ppm; coupling constants J in Hz) (mixture of diastereoisomers in the proportion 65/35): 3.62 (s, 3H), 3.72 (s, 3H), 4.50 (d, J=7.5 1H), 4.50 to 4.70 (large unresolved peak, 1H), 4.62 (broad d, J=7.5, 1H), 4.66

(limit AB, 2H), 5.22 (large unresolved peak, 1H), 5.40 (s, 1H), 5.43 (s, 1H), 7.30 to 7.70 (mt, 5H).

A solution of 1.49 g of lithium hydroxide monohydrate in 40 cm$^3$ of water is added to a solution of 10.48 g of (4S,5R)-5-methoxycarbonyl-4-phenyl-2-trichloromethyl-1, 3-oxazolidine in 120 cm$^3$ of methanol. The solution is stirred at a temperature in the region of 20° C. for 1 hour and the methanol is then evaporated under reduced pressure at 40° C. The residual aqueous phase is then acidified with 35 cm$^3$ of 1M aqueous hydrochloric acid solution. 80 cm$^3$ of ethyl acetate are then added with vigorous stirring. The aqueous phase is withdrawn and extracted again with 80 cm$^3$ of ethyl acetate. The organic phases are combined, dried over sodium sulphate and concentrated to dryness under reduced pressure. The residue obtained is dried overnight at reduced pressure at a temperature in the region of 20° C. There are thus obtained 10.03 g of (4S,5R)-4-phenyl-2-trichloromethyl-1,3-oxazolidine-5-carboxylic acid whose characteristics are the following:

infrared spectrum (CHBr$_3$): characteristic bands at 3380, 3325–2240, 1730, 1600, 1495, 1455, 810 and 760 cm$^{-1}$ proton nuclear magnetic resonance spectrum (200 MHz; d$_6$-DMSO; chemical shifts δ in ppm; coupling constants J in Hz): 4.39 (d, J=7.5, 1H), 4.40 to 4.70 (mt, 2H), 5.13 (mt, 1H), 5.37 (s, 1H), 5.41 (s, 1H), 7.10 to 7.60 (mt, 5H).

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The above references are hereby incorporated by reference.

We claim:
1. An acid of the formula (VII):

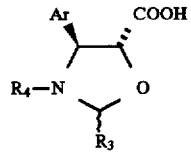

(VII)

in which:
Ar represents a phenyl or α- or β-naphthyl radical unsubstituted or substituted by at least one substituent selected from the group consisting of a halogen atom and an alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, and a trifluoromethyl radical, wherein the alkyl radical and alkyl portions of the other radicals comprise 1 to 4 carbon atoms, the alkenyl and alkynyl radicals comprise 3 to 8 carbon atoms, and the aryl radicals are phenyl or α- or β-naphthyl radicals;

R$_3$ represents a trihalomethyl radical or a phenyl radical substituted by a trihalomethyl radical; and R$_4$ represents a hydrogen atom, a benzoyl radical, or a a radical R$_2$—O—CO— in which R$_2$ represents:
a straight or branched alkyl radical comprising 1 to 8 carbon atoms, an alkenyl radical comprising 2 to 8 carbon atoms, an alkynyl radical comprising 3 to 8 carbon atoms, a cycloalkyl radical comprising 3 to 6 carbon atoms, a cycloalkenyl radical comprising 4 to 6 carbon atoms, or a bicycloalkyl radical comprising 7 to 10 carbon atoms, these radicals being unsubstituted or substituted with at least one substituent selected from the group consisting of a halogen atom, a hydroxyl radical, an alkoxy radical comprising 1 to 4 carbon atoms, a dialkylamino radical in which each alkyl portion comprises 1 to 4 carbon atoms, a piperidino radical, a morpholino radical, a 1-piperazinyl radical (unsubstituted or substituted at position 4 by an alkyl radical comprising 1 to 4 carbon atoms or by a phenylalkyl radical in which the alkyl portion comprises 1 to 4 carbon atoms), a cycloalkyl radical comprising 3 to 6 carbon atoms, a cycloalkenyl radical comprising 4 to 6 carbon atoms, a phenyl radical, a cyano radical, a carboxyl radical, or an alkoxycarbonyl radical in which the alkyl portion comprises 1 to 4 carbon atoms, wherein the cycloalkyl, cycloalkenyl, or bicycloalkyl radicals may be substituted by at least one alkyl radical comprising 1 to 4 carbon atoms;

a phenyl radical unsubstituted or substituted by at least one substituent selected from the group consisting of an alkyl radical comprising 1 to 4 carbon atoms and an alkyloxy radical comprising 1 to 4 carbon atoms; or a saturated or unsaturated nitrogen-containing heterocyclic radical comprising 5 or 6 members, unsubstituted or substituted by at least one alkyl radical comprising 1 to 4 carbon atoms.

2. The acid according to claim 1 in the form of a salt, ester, anhydride, mixed anhydride, or halide.

3. A product of the formula (VIII):

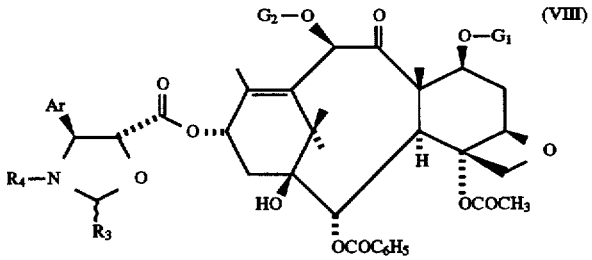

(VIII)

in which:
Ar represents a phenyl or α- or β-naphthyl radical unsubstituted or substituted by at least one substituent selected from the group consisting of a halogen atom and an alkyl, alkenyl, alkynyl, aryl, arylalkyl, alkoxy, alkylthio, aryloxy, arylthio, hydroxyl, hydroxyalkyl, mercapto, formyl, acyl, acylamino, aroylamino, alkoxycarbonylamino, amino, alkylamino, dialkylamino, carboxyl, alkoxycarbonyl, carbamoyl, dialkylcarbamoyl, cyano, and a trifluoromethyl radical, wherein the alkyl radical and alkyl portions of the other radicals comprise 1 to 4 carbon atoms, the alkenyl and alkynyl radicals comprise 3 to 8 carbon atoms, and the aryl radicals are phenyl or α- or β-naphthyl radicals;

R$_3$ represents a trihalomethyl radical or a phenyl radical substituted by a trihalomethyl radical; and R$_4$ represents a hydrogen atom, a benzoyl radical, or a a radical R$_2$—O—CO— in which R$_2$ represents:
a straight or branched alkyl radical comprising 1 to 8 carbon atoms, an alkenyl radical comprising 2 to 8 carbon atoms, an alkynyl radical comprising 3 to 8 carbon atoms, a cycloalkyl radical comprising 3 to 6 carbon atoms, a cycloalkenyl radical comprising 4 to 6 carbon atoms, or a bicycloalkyl radical comprising 7 to 10 carbon atoms, these radicals being unsubstituted or substituted with at least one substituent selected from the group consisting of a halogen atom, a hydroxyl radical, an alkoxy radical comprising 1 to 4 carbon atoms, a dialkylamino radical in which each alkyl portion comprises 1 to 4 carbon atoms, a piperidino radical, a morpholino radical, a 1-piperazinyl radical (unsubstituted or substituted at position 4 by an alkyl radical comprising 1 to 4 carbon atoms or by a phenylalkyl radical in which the alkyl portion comprises 1 to 4 carbon atoms), a cycloalkyl radical comprising 3 to 6 carbon atoms, a cycloalkenyl radical comprising 4 to 6 carbon atoms, a phenyl radical, a cyano radical, a carboxyl radical, or an alkoxycarbonyl radical in which the alkyl portion comprises 1 to 4 carbon atoms, wherein the cycloalkyl, cycloalkenyl, or bicycloalkyl radicals may be substituted by at least one alkyl radical comprising 1 to 4 carbon atoms;

a phenyl radical unsubstituted or substituted by at least one substituent selected from the group consisting of an alkyl radical comprising 1 to 4 carbon atoms and an alkyloxy radical comprising 1 to 4 carbon atoms; or a saturated or unsaturated nitrogen-containing heterocyclic radical comprising 5 or 6 members, unsubstituted or substituted by at least one alkyl radical comprising 1 to 4 carbon atoms; and $G_1$ and optionally $G_2$ represent a protecting group of the hydroxyl functional group.

4. The product according to claim 3, wherein Ar, $R_3$, and $R_4$ are defined as in claim 3, $G_1$ represents a 2,2,2-trichloroethoxycarbonyl or 2-(2-(trichloromethyl)-propoxy) carbonyl radical and $G_2$ represents an acetyl, 2,2,2-trichloroethoxycarbonyl or 2-(2-(trichloromethyl)-propoxy) carbonyl radical.

5. The acid according to claim 1, wherein the halogen atom is fluorine, chlorine, bromine, or iodine.

6. The product according to claim 3, wherein the halogen atom is fluorine, chlorine, bromine, or iodine.

* * * * *